United States Patent [19]

Harryman, II

[11] Patent Number: 5,700,266

[45] Date of Patent: Dec. 23, 1997

[54] SYSTEM FOR REPAIR OF CAPSULO-LABRAL SEPARATIONS

[75] Inventor: Douglas T. Harryman, II, Bellevue, Wash.

[73] Assignee: The University of Washington, Seattle, Wash.

[21] Appl. No.: 824,255

[22] Filed: Mar. 25, 1997

Related U.S. Application Data

[60] Division of Ser. No. 288,629, Aug. 10, 1994, Pat. No. 5,624,446, which is a continuation-in-part of Ser. No. 943,814, Sep. 11, 1992, Pat. No. 5,342,369.

[51] Int. Cl.⁶ ..................................................... A61B 17/56
[52] U.S. Cl. ................................ 606/80; 606/96; 606/223
[58] Field of Search .............................. 606/80, 79, 96, 606/97, 98, 86, 222, 223, 228, 139, 148

[56] References Cited

U.S. PATENT DOCUMENTS

| | | |
|---|---|---|
| 4,599,999 | 7/1986 | Klaue . |
| 4,744,353 | 5/1988 | McFarland . |
| 4,913,137 | 4/1990 | Azer et al. . |
| 4,920,958 | 5/1990 | Walt et al. . |
| 4,946,468 | 8/1990 | Li . |
| 4,961,430 | 10/1990 | Sheahon . |
| 5,030,219 | 7/1991 | Matsen, III et al. . |
| 5,049,150 | 9/1991 | Cozad . |
| 5,133,720 | 7/1992 | Greenberg . |
| 5,139,500 | 8/1992 | Schwartz . |
| 5,180,388 | 1/1993 | DiCarlo . |
| 5,192,293 | 3/1993 | Cartwright et al. . |
| 5,207,753 | 5/1993 | Badrinath . |
| 5,312,412 | 5/1994 | Whipple . |
| 5,437,677 | 8/1995 | Shearer et al. . |

OTHER PUBLICATIONS

"The Spectrum Tissue Repair System Surgical Technique," *Linvatec Corporation* (1992).
E.M. Wolf, M.D., et al., "Arthroscopic Bankart Repair Using Suture Anchors," *Operative Techniques in Orthopaedics*, 1:184–191.
N.J. Maki, M.D., "Arthroscopic Stabilization: Suture Technique," *Operative Techniques in Orthopaedics*, 1:180–183 (1991).
C.D. Morgan, M.D., "Arthroscopic Stabilization: Suture Technique," *Operative Techniques in Orthopaedics*, 1:171–179 (1991).
M.A. Yahiro, M.D., et al., "Arthroscopic Stabilization Procedures for Recurrent Anterior Shoulder Instability," *Orthopaedic Review*, XLVIII:1116–1168 (1989).

*Primary Examiner*—Guy V. Tucker
*Attorney, Agent, or Firm*—Christensen, O'Connor, Johnson & Kindness LLP

[57] ABSTRACT

An elongated drill and suture guide is inserted through a posterior portal during arthroscopic surgery to repair a capsulo-labral separation. The drill and suture guide has a linear longitudinal bore for a drill pin to bore through the glenoid rim of the shoulder joint. A suture guide is inserted through the bore and through the hole in the glenoid rim and through the detached glenoid labrum. A suture is then passed through the guide and is manipulated and tied conventionally to secure the glenoid labrum in approximately the anatomically correct position.

3 Claims, 8 Drawing Sheets

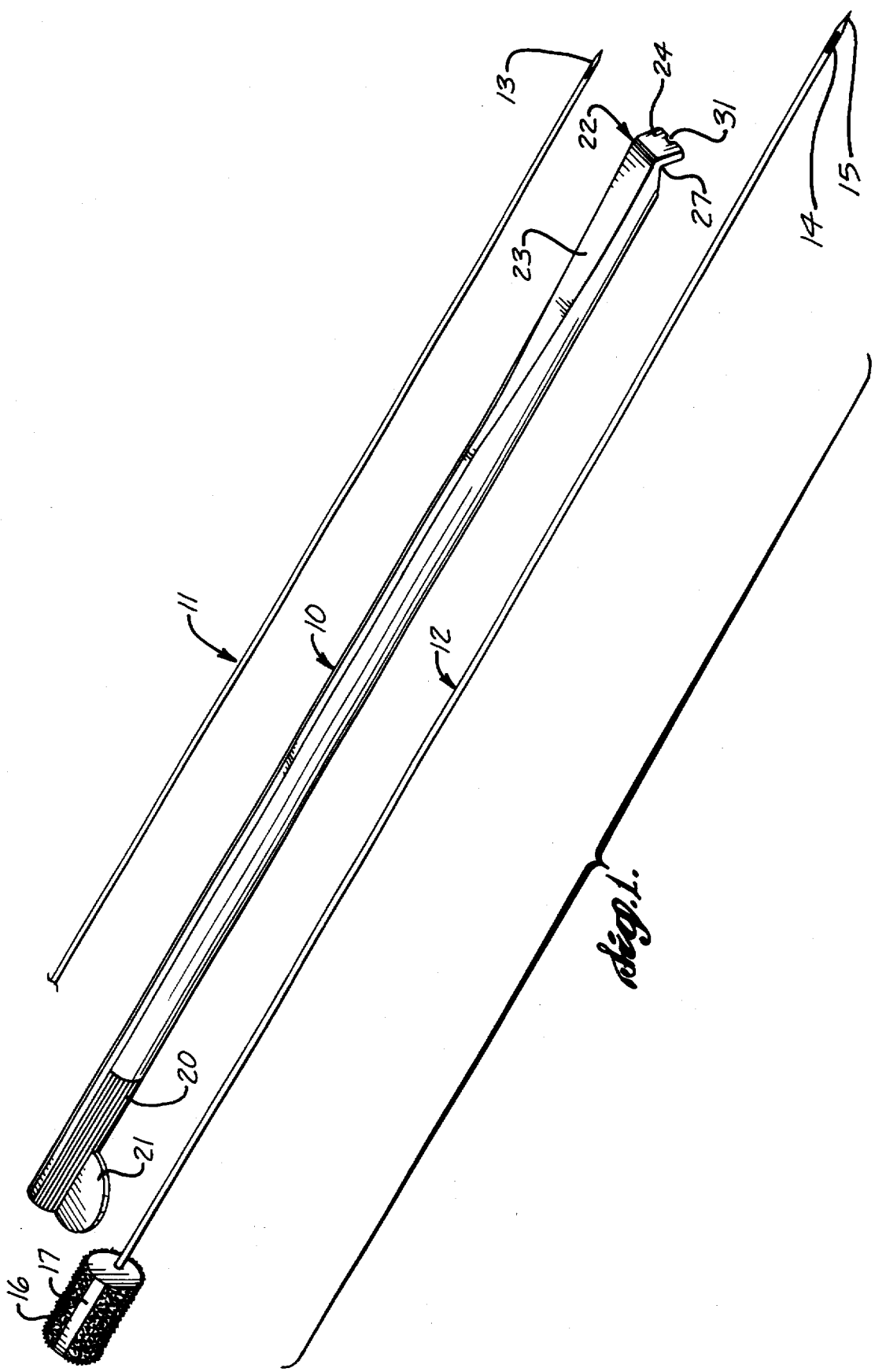

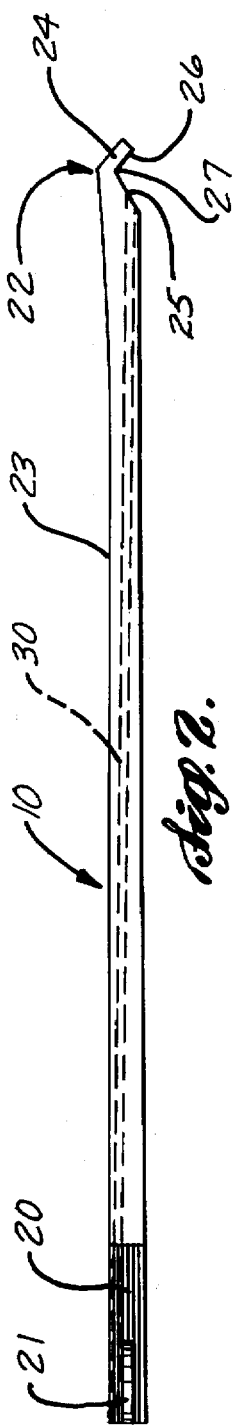
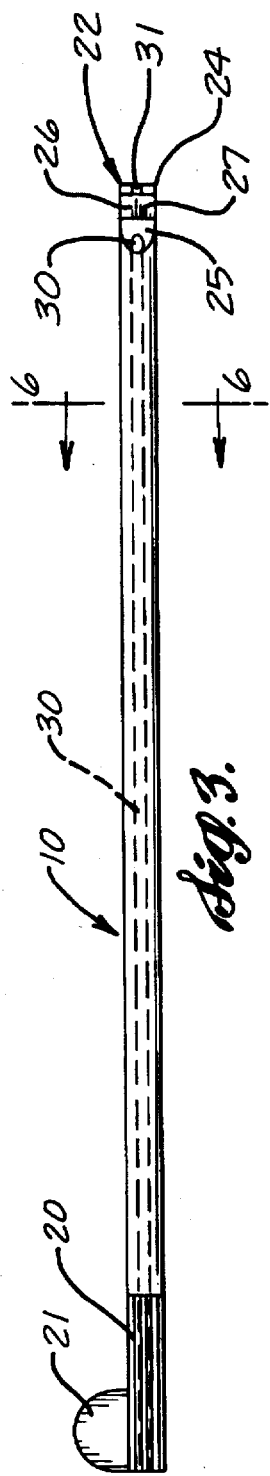
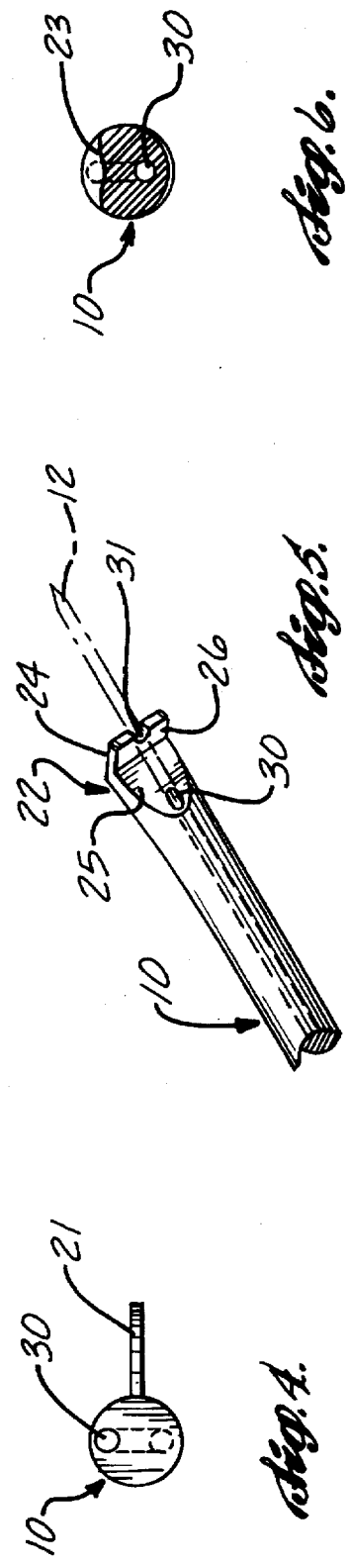
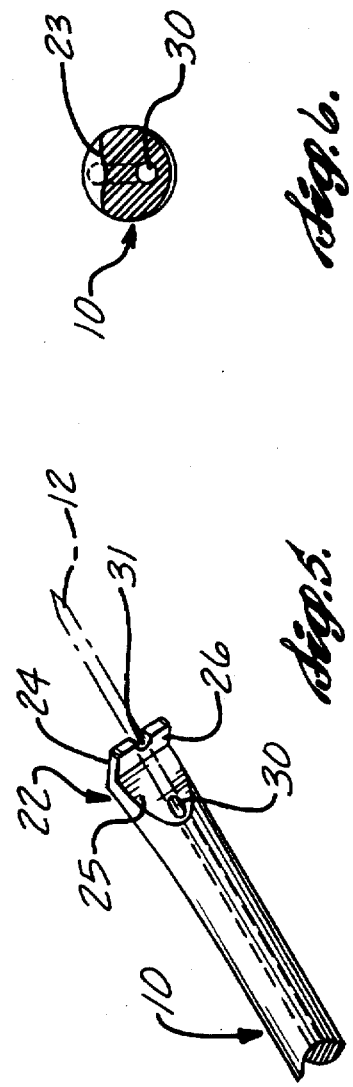

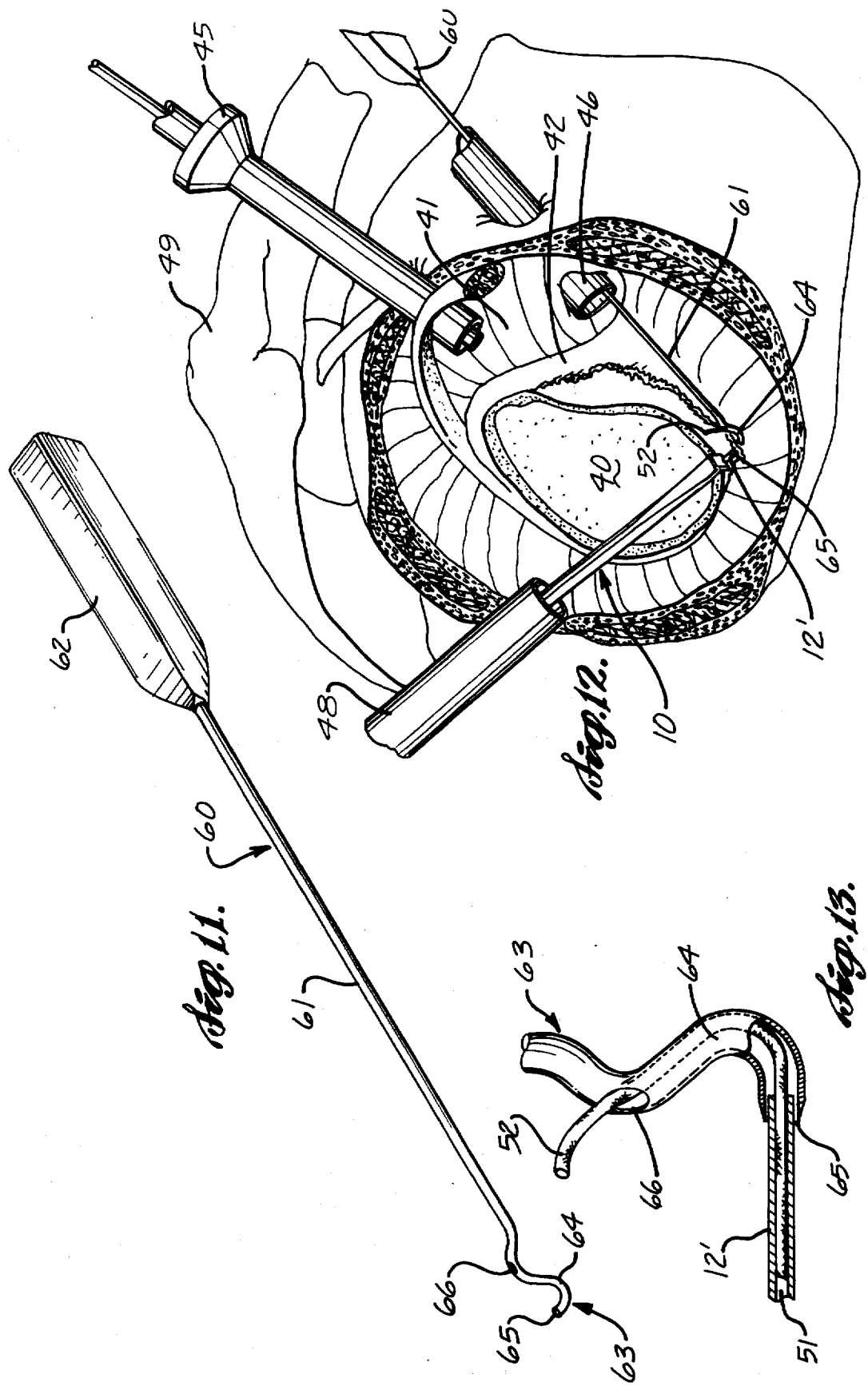

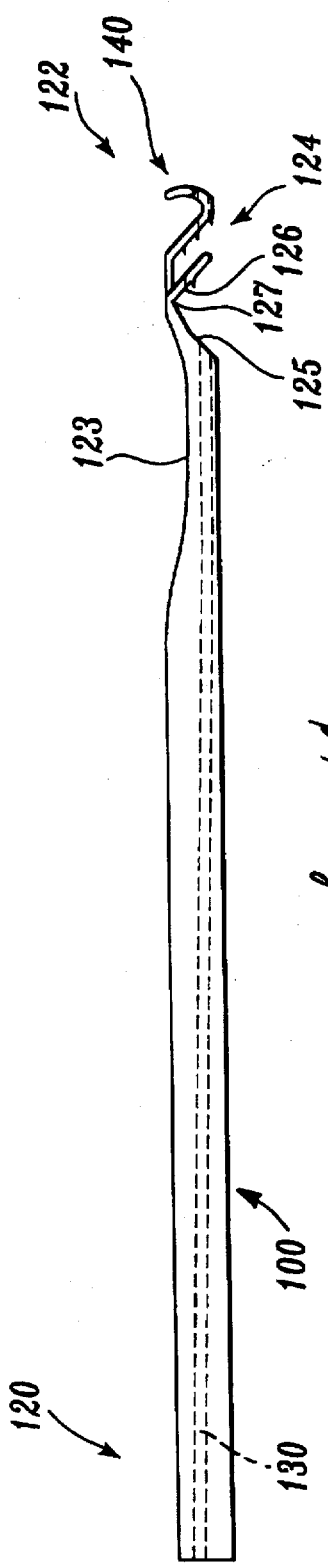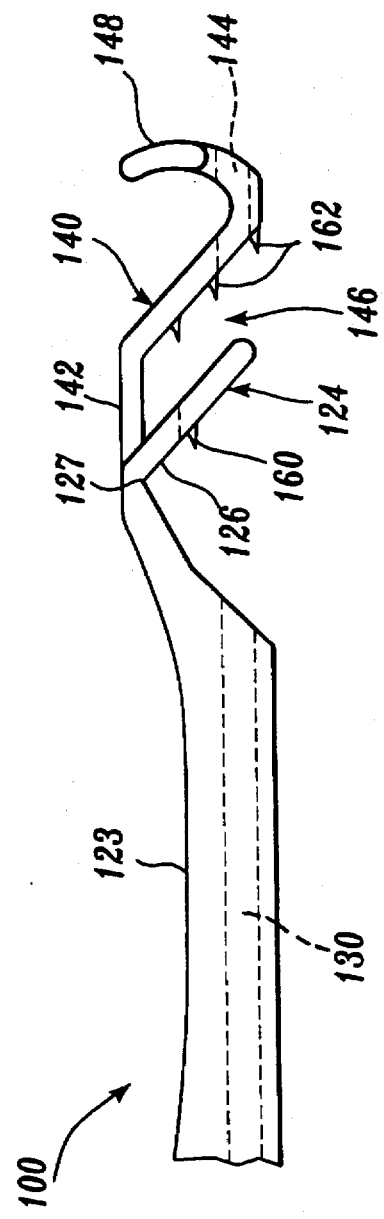

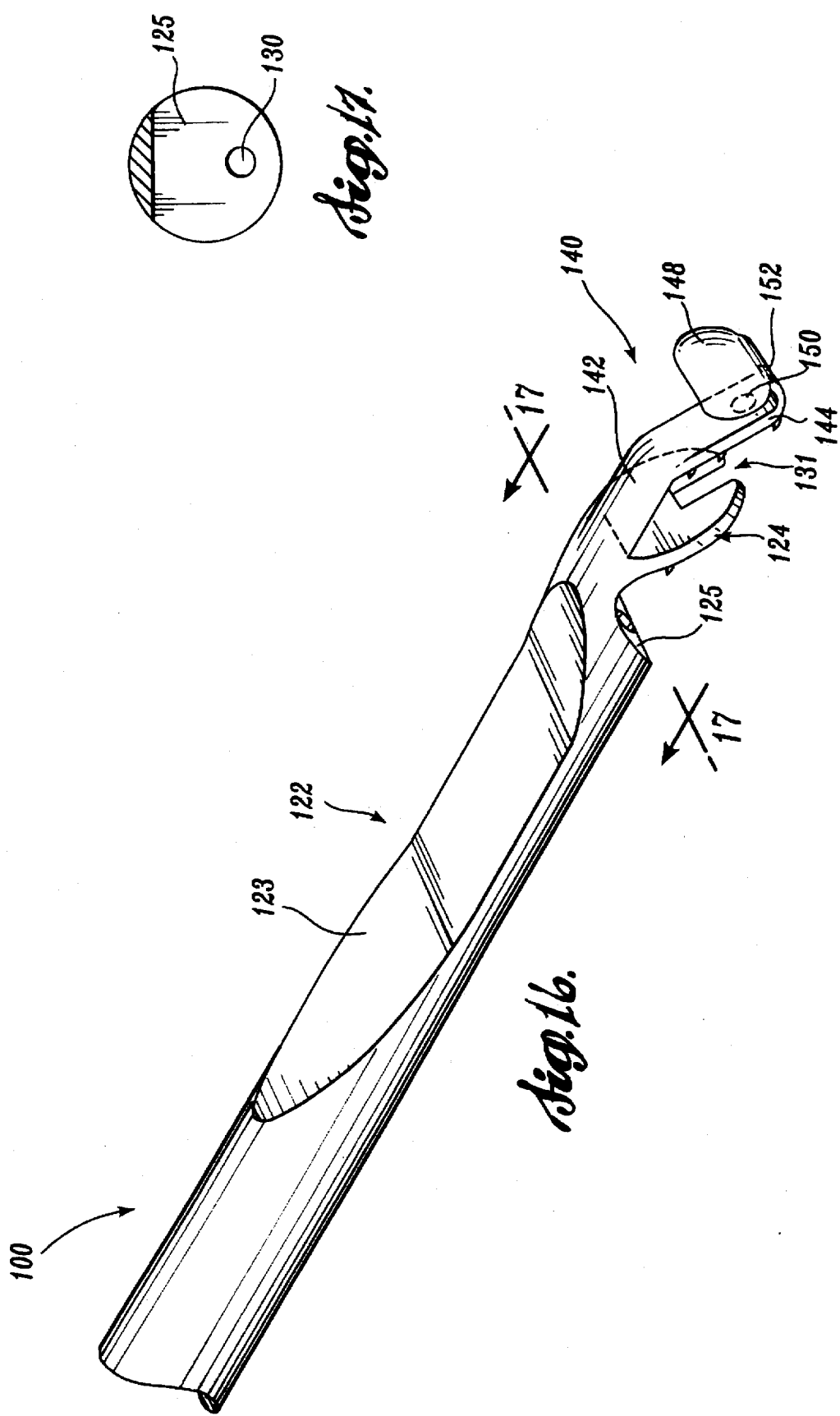

SYSTEM FOR REPAIR OF CAPSULO-LABRAL SEPARATIONS

This is a divisional of the prior application Ser. No. 08/288,629, filed Aug. 10, 1994, which in turn is a continuation-in-part of application Ser. No. 07/943,814, filed on Sep. 11, 1992, now U.S. Pat. No. 5,342,369, the benefit of the filing dates of which are hereby claimed under 35 U.S.C. §120.

FIELD OF THE INVENTION

The present invention relates to the general field of orthopedic instrumentation. More specifically, the present invention relates to an instrument and method for repairing a detachment of connective tissue between the ball and socket of the shoulder joint along the anterior (front) and inferior (lower) margin of the glenoid cavity.

BACKGROUND OF THE INVENTION

The human shoulder articulates about a loose fitting ball-and-socket joint which allows extremely free movement of the arm relative to the trunk. The ball is formed on the head of the humerus (the upper arm bone), and the socket is formed by the shallow, laterally opening glenoid cavity of the scapula (the flat triangular bone in the back of the shoulder). The depth of the socket is increased by a circumferential ring of fibrocartilage, the glenoid labrum, to which the head of the humerus is attached by an encircling mass of connective tissue called the articular capsule. Such capsule includes ligaments and tendons, for example.

There is little area of contact between the ball of the humerus and the glenoid cavity at any time. There always is a considerable part of the ball in contact with the articular capsule. The loose connection allows the articulating surfaces of the bones to be separated substantially. The joint is dependent for its integrity on the surrounding muscles. The joint is so loosely constructed that it is frequently dislocated, particularly by athletes participating in throwing or racquet sports.

There is greater superior (upper) and posterior (rearward) support for the shoulder joint so that it invariably dislocates in an anterior (forward) and inferior (downward) direction. The result is avulsion of the glenoid labrum from the anterior and inferior margins of the glenoid cavity, known as a capsulo-labral separation, one type of which is a Bankart lesion. A capsulo-labral separation can be detected by measuring the range of motion and verifying anterior instability of the shoulder joint.

Nonoperative treatment of anterior shoulder instability is rarely successful, but surgical repair almost always restores stability to the glenohumeral joint. Open shoulder surgery involves spreading the muscles overlying the anterior side of the joint and severing some of the connective tissue to provide access to the anterior glenoid rim. Typically, frayed tissue is resected and all tissue remnants attached to the anterior glenoid rim are debrided. The exposed bone is abraded. In one technique, intersecting holes are drilled in the anterior and lateral faces of the glenoid adjacent to the rim for sutures which secure the detached labrum firmly to the glenoid at two or three locations. Over time the labrum reattaches.

Arthroscopic surgery also is performed for repairing a Bankart lesion. Preparation of the glenoid rim to reduce it to a raw bleeding surface is essentially the same as for open surgery, but different techniques for securing the labrum to the glenoid area are used. In one technique, one or more staples are used to connect the glenoid labrum to the anterior side of the scapular neck medially of the glenoid cavity. In another technique, the labrum is impaled with a rivet which then is driven into the scapular neck. In another technique, blind bores are drilled adjacent to the anterior glenoid rim for specially designed suture anchors. In another technique, a hole is drilled through the scapular neck for suture material or for pins or screws to which suture material can be attached.

Often, full glenohumeral motion and, in the case of an athlete, performance are sacrificed for the stability restored by surgery. It is believed that one reason for inadequate stability, decreased motion and decreased performance is that the glenoid labrum is not secured at the anatomically correct location by use of known instruments and procedures. In some of the known techniques the labrum is secured to a single location such as an anchor member in the anterior side of the scapular neck, and in other known procedures the labrum is attached at two or three locations along only the anterior portion of the glenoid rim. Nevertheless, dislocation of the shoulder joint will tear the glenoid labrum from the inferior rim, as well as the anterior rim. Access to the inferior glenoid rim is limited, particularly during arthroscopic surgery. There is no known arthroscopic system that allows securing the labrum directly to the inferior glenoid rim, in addition to securing it along the anterior rim, so that the labrum will reattach in the correct position.

SUMMARY OF THE INVENTION

The present invention provides a system for repair of capsulo-labral separations such as Bankart lesions to correct anterior shoulder instability. The system uses a novel orthopedic instrument in the form of an elongated drill and suture guide which may be inserted during arthroscopic surgery such that a recess on the distal end of the guide fits over the glenoid rim in the area of the lesion. Unlike traditional arthroscopic shoulder surgery in which access to the glenoid rim is from the front, the instrument is inserted through a posterior portal and then between the ball of the humerus and the glenoid cavity so that access to both the anterior and inferior glenoid rim is possible. The instrument has a linear longitudinal bore opening into the distal recess for a drill pin effective to bore through the glenoid rim by bridging across the recess. With the instrument held stationary, the drill pin is removed and a suture passer is inserted through the bore of the instrument and through the hole in the glenoid rim, then through the detached glenoid labrum, which may be held in the anatomically correct location by a tissue grasper or in an additional groove or recess in the drill and suture guide itself. Alternatively, a hooked suture guide is used to penetrate the labrum at the desired location and convey suture material from the suture passer through the labrum. Thereafter, the suture is manipulated and tied conventionally to secure the glenoid labrum in approximately its anatomically correct position, whereupon the drill and suture guide is reinserted for repeating the procedure at another location along the lesion.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 1 is a top perspective of instruments used in a system for repairing capsulo-labral separations in accordance with the present invention including a conventional drill pin, a conventional suture passer, and a novel drill and suture guide for the conventional pin and passer.

FIG. 2 is a side elevation of the drill and suture guide of FIG. 1.

FIG. 3 is a bottom plan of the drill and suture guide of FIG. 1.

FIG. 4 is a proximate end elevation of the drill and suture guide of FIG. 1.

FIG. 5 is an enlarged bottom perspective of the distal end portion of the drill and suture guide of FIG. 1.

FIG. 6 is a transverse section along line 6—6 of FIG. 3.

FIG. 11 is a top perspective of a novel suture guide that can be used in the system of the present invention.

FIG. 12 is a perspective corresponding to FIG. 7 illustrating use of the suture guide of FIG. 11.

FIG. 13 is an enlarged detail of the distal end portion of the suture guide of FIG. 11 during use, with parts broken away and parts shown in section.

FIG. 14 is a side elevation of an alternate drill and suture guide of the present invention.

FIG. 15 is an enlarged side elevation of the distal end portion of the drill and suture guide of FIG. 14.

FIG. 16 is an enlarged top perspective of the distal end portion of the drill and suture guide of FIG. 14.

FIG. 17 is a transverse section along line 17—17 of FIG. 16.

DETAILED DESCRIPTION OF THE PREFERRED EMBODIMENT

Figure 10:
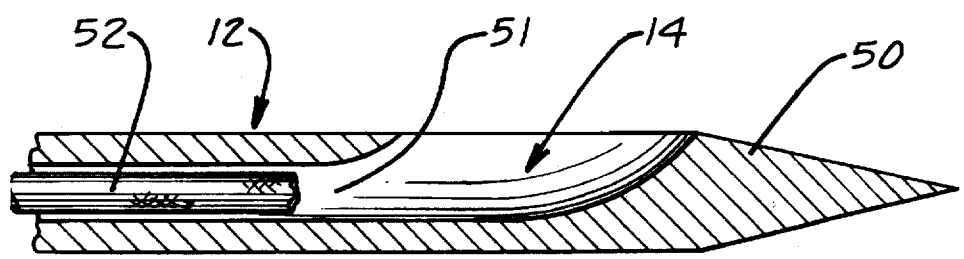
FIG. 10 (on the drawing sheet with FIG. 7) is an enlarged longitudinal section of the distal end portion of the suture passer shown in FIG. 1.

The system in accordance with the present invention is used to repair a capsulo-labral separation such as a Bankart lesion, i.e., to secure the fibrocartilage periphery known as the glenoid labrum to the glenoid rim at approximately the anatomically correct location after the labrum has been torn from the rim by dislocation of the shoulder joint. Instruments used in the system in accordance with the present invention are shown in FIG. 1 and include a novel drill and suture guide 10 having a longitudinally extending bore for receiving a conventional drill pin 11 or a novel suture passer 12. Pin 11 has a sharpened distal end 13 and a proximate end (not shown) for fitting in the chuck of a conventional drill.

Suture passer 12 has a longitudinal bore communicating with a side port 14 adjacent to the solid pointed distal end 15 of the suture passer. The other end of the bore opens through the proximate end of the passer. The proximate end portion 16 is enlarged and has a knurled surface for ease in manipulation of the passer. The enlarged proximate end portion 16 has a longitudinally extending flattened portion 17 registered axially with the side port 14 so that the user always knows the direction of opening of the side port.

The drill pin 11 and suture passer 12, except for the enlarged proximate end portion 16 of the suture passer, are of a diameter small enough to pass through the bore of the drill and suture guide 10.

With reference to FIGS. 2 through 6, one drill and suture guide 10 in accordance with the present invention is an elongated shaft having a proximate handle end portion 20 which preferably is knurled and includes a short radially extending tab 21 for ease in holding and manipulating the instrument. From the tab forward, the maximum diameter of the shaft is sufficiently small so as to fit through a standard arthroscopic sleeve, preferably no greater than about 5 to 6 mm. For use in the present invention, the shaft can be about seven inches long.

Except for the radially extending tab 21, the shaft is substantially cylindrical throughout the major portion of its length, from the proximate end portion 20 toward the distal or working end portion 22. However, as seen in FIG. 1 and FIG. 2, the upper surface of the distal end portion of the instrument is flattened and curved gradually upward from the cylindrical proximate and central portions of the shaft. As seen in FIG. 6, the flattened distal top surface 23 also is preferably slightly concave in cross section.

The distal tip of the instrument is formed by a short flange 24 inclined downward from the top of the shaft. Just proximate to the flange, the end of the instrument is beveled to form an upward inclined surface 25 facing the downward inclined surface 26 of the flange 24. Such surfaces meet at an abrupt corner 27 extending transversely of the instrument. Preferably, the beveled surface 25 makes a small acute angle of about 30° relative to the center line of the instrument, whereas the inner surface of the flange makes a greater acute angle of about 40° to 45° relative to the center line of the instrument. Consequently, the angle between the planar facing surfaces is obtuse, preferably about 110°. In the preferred embodiment, the flange 24 is about 4 mm long and about 2 mm thick, so that the lower tip of the flange is positioned at or slightly below the center line of the shaft of the instrument.

The shaft of the drill and suture guide has a linear through bore 30, which preferably is about 2 mm in diameter. Bore 30 extends obliquely relative to the center line of the instrument, starting at a location offset upward from the center of the instrument at the distal end, as seen in FIG. 4, and ending at a location offset downward from the center line of the instrument as seen in FIG. 5 and FIG. 6. The distal end of bore 30 opens closely adjacent to the bottom of the beveled surface 25. The axis of the bore traverses the recess defined by the facing surfaces 25 and 26 and passes just beneath the bottom tip of the flange 24. As seen in FIG. 5, the bottom tip of flange 24 can have a central notch 31, so as not to interfere with extension of the drill pin or suture passer through the bore 30 and across and beyond the recess.

Figure 7:
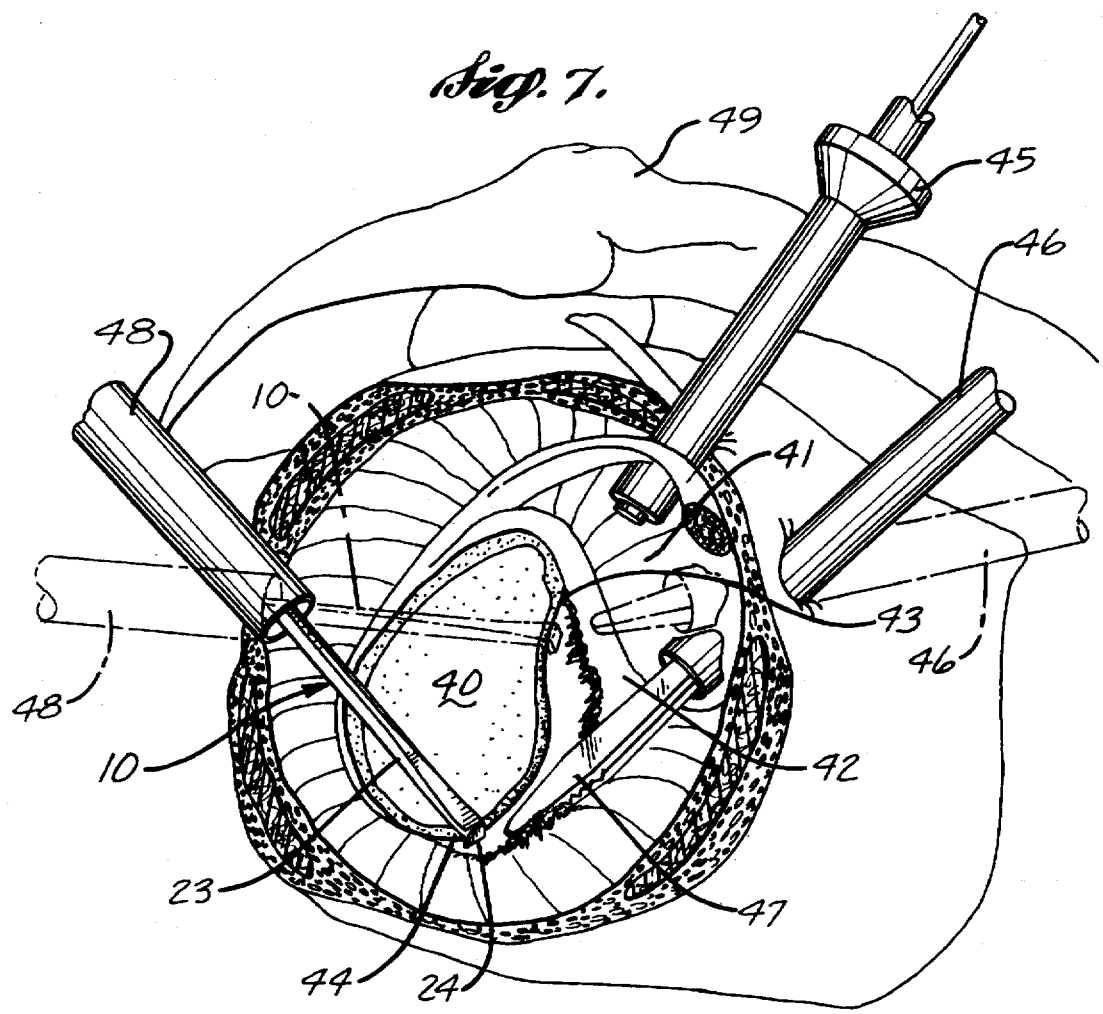
FIG. 7 is a somewhat diagrammatic perspective of a shoulder joint during arthroscopic surgery looking generally medially and posteriorly toward the glenoid cavity with the humerus and other body parts deleted.

FIG. 7 illustrates the anatomy in the area of a capsulo-labral separation repairable by use of the system in accordance with the present invention. The scapular side of the shoulder joint is illustrated as viewed in a medial direction with the humerus and other adjacent tissue deleted. The shallow glenoid cavity 40 is normally encircled by the articular capsule 41 of connective tissue attached at the margin of the cavity by the glenoid labrum 42. In the case of shoulder dislocation, a lesion results where the labrum is torn from the anterior rim 43 and inferior rim 44.

For arthroscopic viewing of the affected area, a generally downward-directed portal is opened just anterior to the supraspinatus tendon for a conventional cannula 45. Another anterior portal is opened for a cannula 46 passing just above the upper border of the subscapularis tendon, lateral to the middle glenohumeral ligament. Cannula 46 provides access to the area of the lesion for conventional instruments, such as a tissue grasper 47. A posterior portal is opened for a generally forward-directed cannula 48 at a location just inferior to the postero-lateral corner of the acromion 49. The forwarded-directed cannula 48 provides access to the affected area by the drill and suture guide 10 in accordance with the present invention.

As is conventional, frayed tissue obscuring arthroscopic viewing of the labrum and glenoid rim is resected. All tissue remnants attached to the glenoid rim in the area of the tear are debrided so that the bone of the rim is exposed adjacent to the separated labrum. A burr and/or rasp is used to abrade the inner and outer margins of the glenoid rim. The resection, debriding and abrading all are under direct arthroscopic visualization and can be accomplished by access through the posterior portal as well as through the anterior portals.

Next, the drill and suture guide 10 is inserted through the posterior portal and is positioned with its distal flange 24 hooked over the raw bony surface of the inferior glenoid rim. The beveled distal surface of the instrument through which its bore opens is placed flat against the rim, which helps to stabilize the instrument. In addition, the flattened and preferably concave upper surface 23 is engaged by the adjacent ball of the humerus which presses against the top of the instrument and helps to maintain it stably in position. If the distal end portion of the upper surface of the instrument were cylindrical, as is the majority of the shaft, localized pressure would be applied against the articular cartilage of the humeral ball which could damage the cartilage and dislodge the instrument.

Figure 8:
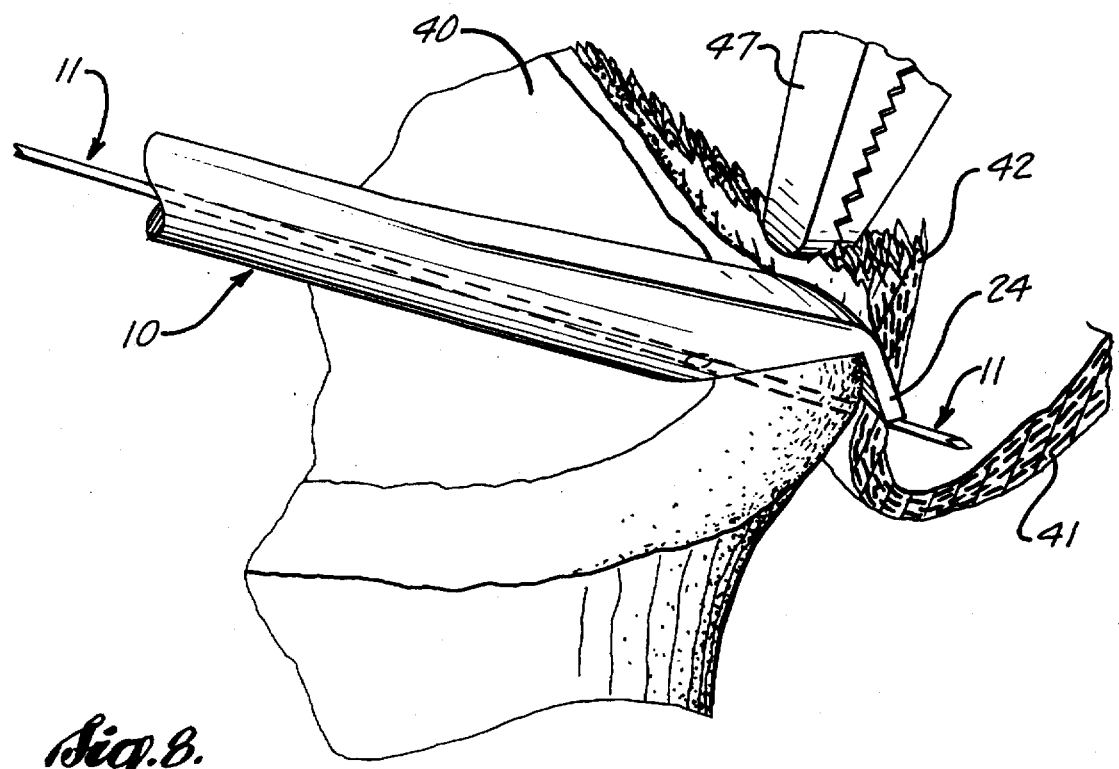
FIG. 8 is an enlarged perspective looking generally medially and superiorly of such joint illustrating one step of the system in accordance with the present invention.

With reference to FIG. 8, with the drill and suture guide 10 held firmly in position as described above, a section of the separated labrum is grasped and held against the glenoid rim in approximately the anatomically correct position. The drill pin 11 is inserted through the bore of guide 10. Conventional external drilling equipment is used to rotate and advance the drill pin linearly through the margin of the bone from inside the glenoid cavity to the anterior side of the bone just below the rim. The drill pin passes just below the bottom of the flange 24 through its central notch, as represented in FIG. 5.

Figure 9:
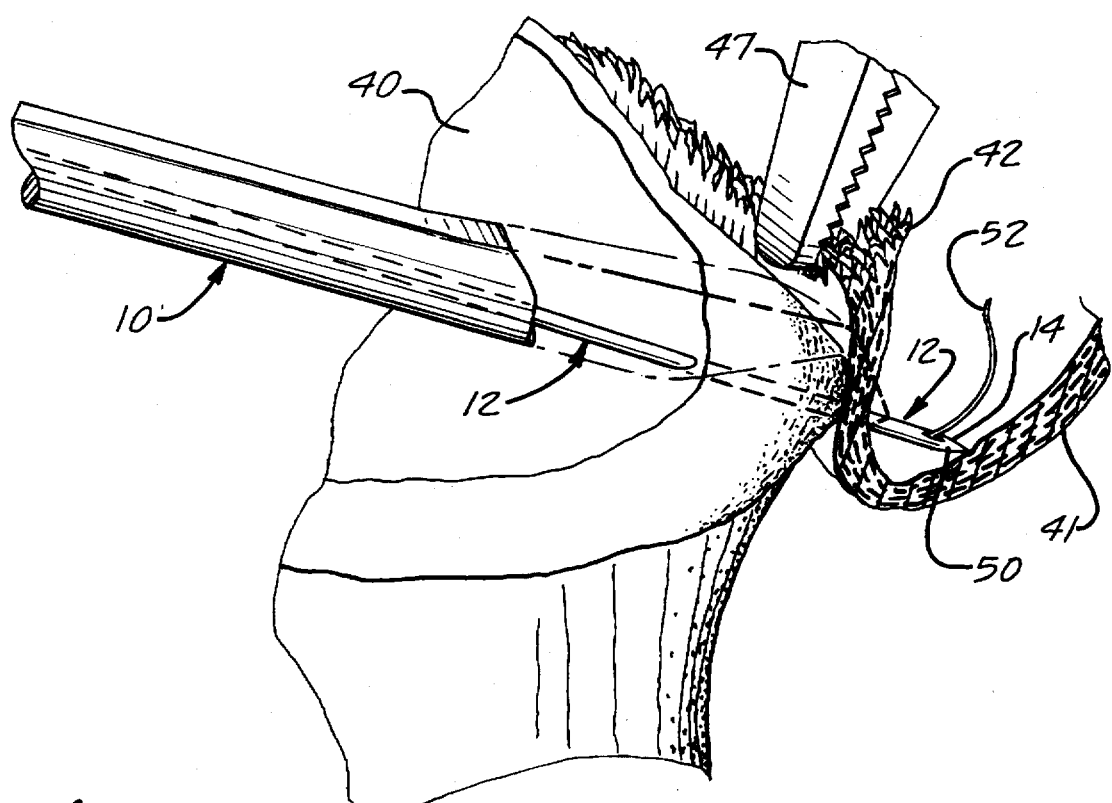
FIG. 9 is a perspective of such joint corresponding to FIG. 8 but illustrating another step of such system.

The drill pin 11 is removed and, without changing the position of the guide 10, the suture passer 12 is inserted through the bore of the guide so as to pass through the newly-drilled hole in the glenoid rim. Suture material 52 is threaded through the bore of the passer so that an end of the suture material projects from the side port 14 as seen in FIG. 9. With reference to FIG. 10 (on the drawing sheet with FIG. 7), the tip 50 of the suture passer 12 is solid and pointed, and the bore 51 of the suture passer curves gradually outward to the side port 14 which is of a length substantially greater than the diameter of the straight portion of the bore for free passage of the end of the suture material through the side port. Such suture end can be grasped by an appropriate implement fed through the inferior anterior portal, whereupon the suture passer and guide 10 can be retracted from the posterior portal. If the appropriate part of the labrum cannot be penetrated by the suture passer, a conventional suture hook can be used. A grasping implement then is inserted through the posterior portal to retrieve the loose end of suture material and bring it to the exterior of the posterior cannula for tying of a conventional fisherman's knot (slip knot) which then is advanced back through the posterior portal by a conventional knot pusher and tightened to secure the labrum in the approximate anatomically correct position.

It can be difficult to suture the labrum at the desired location using the instruments described above. An alternative is to use a special suture guide of the type illustrated in FIG. 11 with a conventional suture passer of the type having an exit port in its distal end in line with the bore of the suture passer. The special suture guide 60 has an elongated central shank 61 extending from an angular handle 62 forming the proximate end portion of the guide. The shank leads to a pig-tailed distal end portion 63, including at least one full generally helical loop 64. The pig-tailed portion of the guide has a central bore opening at the distal end 65, and extending proximally through the helical loop to a circumferential outlet port 66.

The apertured distal end 65 of the pig-tailed suture guide 60 is sharpened. The distal end portion and central shank of the guide are of a maximum diameter no greater than about 6 mm so that they can be fitted through the anterior inferior cannula 46 as illustrated in FIG. 12. Such sharpened distal end can be manipulated to penetrate the labrum at the desired anatomically correct location with the aperture of the distal end exposed adjacent to the straight suture passer 12'. As illustrated in FIG. 13, the suture passer 12' and pig-tailed suture guide 60 are positioned such that the distal end portion of the suture passer is received in the distal end 65 of the suture guide. The labrum and connective capsular tissue attached to it are hooked in the loop 64 of the helix of the guide. Suture material 52 then can be passed through the straight bore of the passer 12' into the curved bore of the guide 60 such that the suture material is conveyed through the labrum and out through the circumferential port 66 of the guide. The guide then is removed from the inferior anterior cannula, leaving the inner end portion of the suture material exposed for grasping implements. The suture material is brought to the exterior of the posterior cannula for tying, knot-pushing and tightening, as described above.

With reference to FIG. 7, regardless of the suturing system used, the procedure of securing the separated labrum to the prepared raw bony surface of the glenoid rim is repeated at higher locations all the way up to and including the anterior portion 43 of the rim, as represented in broken lines in FIG. 7. Consequently, substantially the full extent of the labrum can be secured at the anatomically correct position. In comparison, previous arthroscopic repair techniques rely on access to the glenoid cavity from the front and do not secure the separated labrum directly to the inferior rim 44. Some techniques are more anatomically correct than others, such as those which secure the labrum at several locations along the length of the anterior rim with implantable anchors as compared to those which secure the labrum only to one or two locations in the scapular neck medially of the glenoid cavity. Nevertheless, no prior method is known which allows direct securing of the inferior portion of the labrum to the inferior glenoid rim and, more particularly, securing the inferior labrum by suturing without staples, screws or anchoring members of metal or other foreign material. When the labrum cartilage reattaches to the glenoid rim, the glenohumeral connective tissue in the anatomically correct position, including ligaments and tendons, should reduce the chance of recurrent instability in addition to permitting a more natural range of motion and performance close to that experienced prior to dislocation of the shoulder.

FIGS. 14–17 illustrate an alternate drill and suture guide of the invention. The structure and use of the alternate embodiment of the drill and suture guide to repair capsulolabral separations is similar to the embodiment described above and features of the alternate embodiment not discussed below may be understood by reference to the discussion of the first embodiment.

With reference to FIG. 14, an alternate drill and suture guide 100 in accordance with the present invention is an elongated shaft having a proximate handle end portion 120 which may include a radially extending tab or enlarged handle (not shown) for ease in holding and manipulating the instrument in a manner similar to the first embodiment described above. As with the first embodiment, the maximum diameter of the shaft is sufficiently small so as to fit through a standard arthroscopic sleeve, preferably no greater than about 5 to 6 mm. For use in the present invention, the shaft can be about seven inches long.

The shaft is substantially cylindrical throughout the major portion of its length, from the proximate end portion 120 toward the distal or working end portion 122. However, as best seen in FIGS. 15 and 16, the upper surface 123 of the distal end portion of the instrument is flattened and concave, curving gradually downward and then upward from the cylindrical proximate and central portions of the shaft. In a manner similar to the first embodiment, the flattened distal top surface 123 may also be slightly concave in cross section.

The distal end of the instrument includes a short flange 124 inclined downward from the top of the shaft. Just proximate to the flange 124, the end of the instrument is beveled to form a biangular, upward inclined surface 125 facing the downward inclined surface 126 of the flange 124 to form a transverse recess. Such surfaces meet at an abrupt, slightly rounded corner 127 extending transversely of the instrument. Preferably, the biangular surface 125 makes a small acute angle of about 30° relative to the center line of the instrument, whereas the inner surface of the flange 124 makes a greater acute angle of about 40 to 45° relative to the center line of the instrument. Consequently, the angle between the planar facing surfaces is obtuse.

The distal end portion 122 of the instrument terminates at an extension or proboscis 140 that extends distally from the top of the flange 124. The proboscis includes a first section 142 that extends axially from the flange and a second section or flange 144 that inclines downward approximately parallel to flange 124 to form a capture recess or groove 146 between the two flanges 124 and 144. From the bottom of the second flange 144 the neck 147 of a spreader 148 curves upward to an enlarged head 149 which, from its central portion attached to the neck 147, can be curved slightly proximately such that the distal end of the instrument is slightly convex as best seen in FIG. 16. Head 149, neck 147 and the second flange 144 define a transverse recess on the opposite side of the shaft from the capture recess or groove 146.

A single tooth 160 protrudes proximately from the inclined surface 126, and a plurality of teeth 162 protrude proximately from the inner surface of the second flange 144 into the capture recess or slot 146. In alternate embodiments, differing numbers of teeth having differing sizes and shapes could be used.

The shaft of the drill and suture guide 100 has a linear through bore 130, which preferably is about 2 mm in diameter. Bore 130 extends obliquely relative to the center line of the instrument, starting at a location offset upward from the center of the instrument at the distal end, as seen in FIG. 14, and ending at a location offset downward from the center line of the instrument as seen in FIG. 14 and FIG. 17. The distal end of bore 130 opens closely adjacent to the bottom of the beveled surface 125 as best seen in FIG. 17. The axis of the bore traverses the recess defined by the facing surfaces 125 and 126 and passes through a central notch or slot 131 in the flange 124, a hole 150 in the second flange 144 and a hole 152 in the spreader 148 (FIG. 16), so as not to interfere with extension of the drill pin or suture passer through the distal end of the instrument.

The alternate drill and suture guide 100 is used similarly to the first described embodiment. In the same manner described with respect to the first embodiment, an anterior portal is opened for arthroscopic viewing. Another anterior portal is opened to provide access to the area of the lesion or separation. A posterior portal is opened for access to the affected area by the drill and suture guide 100. The frayed tissue and the glenoid rim are prepared in the same manner described with respect to the first embodiment.

Figure 18:
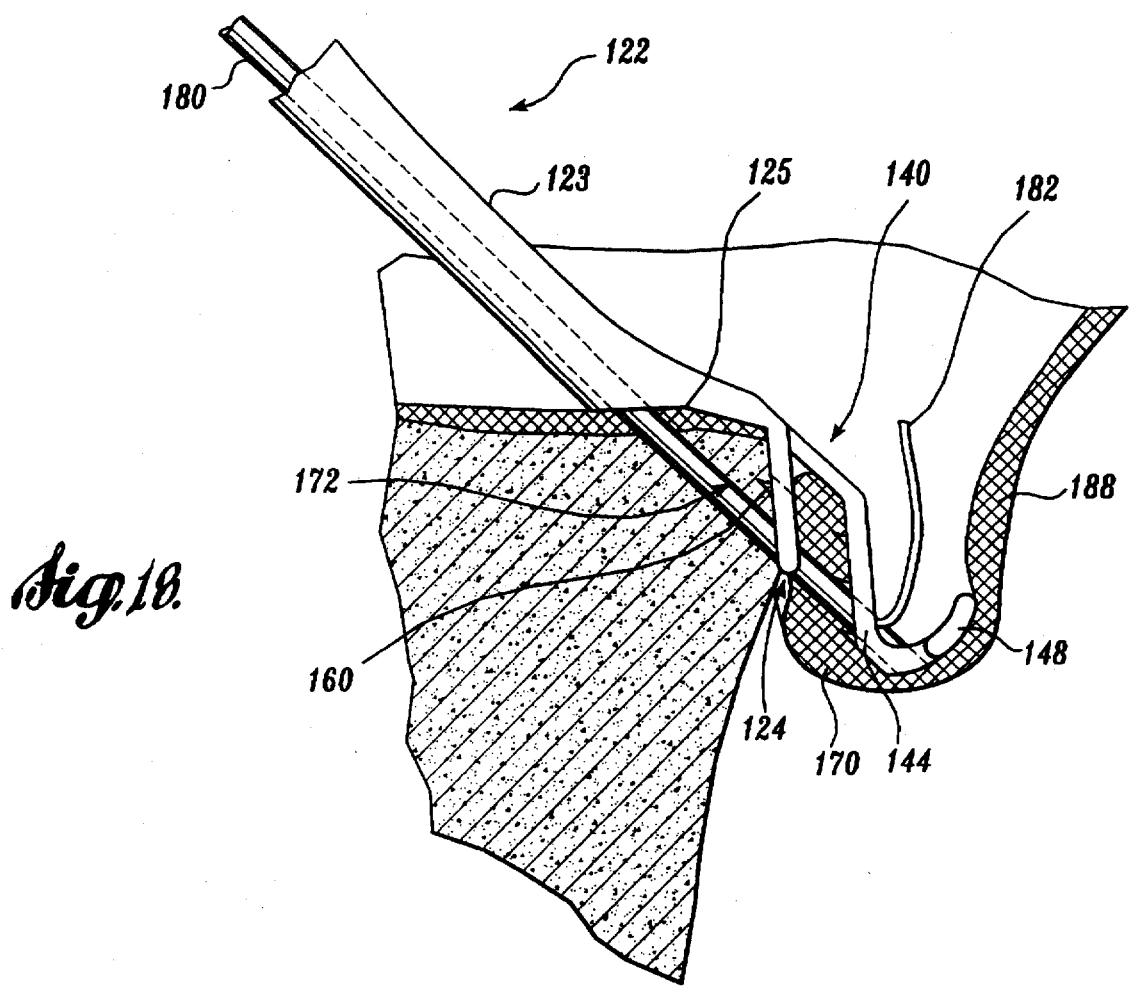
FIG. 18 is a somewhat diagrammatic cross section of a shoulder joint illustrating the alternate drill and suture guide of FIG. 14 in use during one step of the method of the invention.

The drill and suture guide 100 is then inserted through the posterior portal and positioned as shown in FIG. 18 with the flange 124 hooked over the raw bony surface of the glenoid rim 172. The biangular surface 125 more closely approximates the shape of the outer margin of the glenoid cavity, and the facing surface 124 is placed against the glenoid rim such that the tooth 160 bites into the bone to help stabilize the instrument. In addition, the upper surface 123 of the instrument is engaged by the adjacent ball of the humerus which presses against the top of the instrument and helps to maintain it stably in position.

Rather than holding the torn labrum 170 with a tissue grasper during drilling and suture passing, the torn labrum is inserted into the capture recess or groove 146 using a conventional grasper or other instrument, either before or after the drill guide 100 is positioned. The teeth 162 engage the captured glenoid labrum 170 as it is inserted into the capture slot and help to maintain it in position With the drill and suture guide 100 held firmly in position as described above, a drill pin (not shown) is inserted through the bore of guide 100. As with the first embodiment, the drill pin is used to drill linearly through the margin of the bone from inside the glenoid cavity to the anterior side of the bone just below the rim, and also through the captured labrum. The drill pin is removed and, without changing the position of the guide 100, a side port suture passer 180 is inserted through the bore of the guide so as to pass through the newly-drilled hole in the glenoid rim. The suture passer also passes through the flange 124, glenoid labrum 170, and second flange 144. Suture material 182 is threaded through the bore of the suture passer so that an end of the suture material projects from a side port (not shown) as seen in FIG. 18.

The head 149 of the proboscis 140 helps to push the tissue of the articular capsule 188 away from the suture material, thus allowing the suture to be easily threaded through the suture passer and seized by a grasper. Pushing the tissue of the articular capsule away also allows the surgeon to more easily see the suture during the threading and grasping process. In addition, positioning the glenoid labrum in the capture recess or slot 146 during suturing insures that sutures are placed at an appropriate distance from the free (torn) end of the glenoid labrum.

Figure 19:
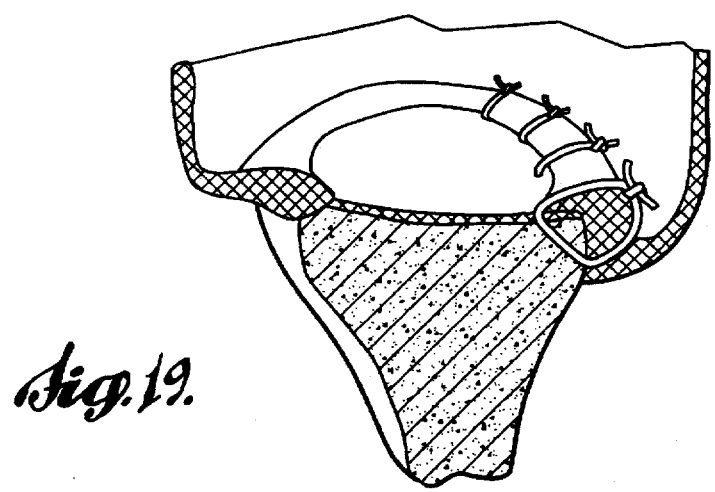
FIG. 19 is a top perspective, partial cross section of the glenoid and articular capsule after reattachment using the method of the invention

The drill and suture guide 100 is then removed while the end of the suture material is held by a grasper or similar instrument. After removing the guide 100, the loose ends of the suture material are tied using a conventional fisherman's knot (slip knot) and tightened to secure the labrum in the approximate anatomically correct position, as shown in FIG. 19 which illustrates the reattachment of the labrum after several sutures along the length of the separation.

While the preferred embodiment of the invention has been illustrated and described, it will be appreciated that various changes can be made therein without departing from the spirit and scope of the invention. For example, the proboscis could be formed as a discrete part that is slidably or otherwise movably attached to the shaft. The proboscis could then be slidably moved back and forth in order to alter the size of the capture recess or slot, to assist in capturing and clamping the free end of the glenoid labrum.

The embodiment of the invention in which an exclusive property or privilege is claimed are defined as follows:

1. The method of repairing a capsulo-labral separation which comprises opening a posterior portal for access to the shoulder joint affected by the separation, inserting a drill guide through the posterior portal and between the affected glenoid cavity and humeral ball, fitting a transverse of the drill guide over the rim of the glenoid cavity at the side of the glenoid cavity generally opposite from the portal, passing a drilling implement through a longitudinal bore of the drill guide for bridging across the recess and for penetrating through the portion of the rim received in the recess to form a hole therethrough, and suturing the separated labrum in the area of the lesion to such hole.

2. The method defined in claim 1, including holding a portion of separated labrum with a tissue grasper adjacent to the area of the rim of the glenoid cavity engaged by the drill guide prior to passing a drilling implement through the longitudinal bore of the drill guide, such that the drilling implement passes through both the portion of the rim received in the drill guide recess and the separated labrum.

3. The method of repairing a capsulo-labral separation which comprises opening a posterior portal for access to the shoulder joint affected by the separation, inserting a drill guide through the posterior portal and between the affected glenoid cavity and humeral ball, fitting a first transverse recess of the drill guide over the rim of the glenoid cavity at the side of the glenoid cavity generally opposite from the portal, firing a portion of separated labrum in a second transverse recess of the drill guide adjacent to the first recess in the area of the rim of the glenoid cavity engaged by the drill guide, passing a drilling implement through a longitudinal bore of the drill guide for bridging across the first recess and the second recess and for penetrating through the portion of the rim received in the first recess to form a hole therethrough and through the portion of the labrum received in the second recess, and suturing the separated labrum in the area of the lesion to the hole through the rim of the glenoid cavity.

* * * * *

UNITED STATES PATENT AND TRADEMARK OFFICE
CERTIFICATE OF CORRECTION

PATENT NO. : 5,700,266
DATED : December 23, 1997
INVENTOR(S) : D.T. Harryman, II It is certified that error appears in the above-indentified patent and that said Letters Patent is hereby corrected as shown below:

| COLUMN | LINE | |
|---|---|---|
| On title page, [56] col. 2 | Refs. Cited (Other Publs., Item 2) | "1:184-191." should read --1:184-191 (1991).-- |
| [56] col. 2 | Refs. Cited (Other Publs., Item 5) | "XLVIII:1116-1168" should read --XVIII:1161-1168-- |
| Column 9 | 16 | "embodiment" should read --embodiments-- |
| 9 (Claim 1, | 22 line 5) | After "transverse" insert --recess-- |
| 10 (Claim 3, | 16 line 8) | "firing" should read --fitting-- |

Signed and Sealed this

Twenty-first Day of April, 1998

Attest:

BRUCE LEHMAN

*Attesting Officer*          *Commissioner of Patents and Trademarks*